United States Patent [19]

Siman et al.

[11] Patent Number: 5,171,545
[45] Date of Patent: Dec. 15, 1992

[54] APPARATUS AND METHOD FOR DECONTAMINATION OF MICROSPHERES USED IN A FLUIDIZED PATIENT SUPPORT SYSTEM

[75] Inventors: Alfred W. Siman, Charlotte, N.C.; Richard B. Stacy, Charleston, S.C.; W. Layne Carruth, Bartlett, Tenn.

[73] Assignee: SSI Medical Services, Inc., Charleston, S.C.

[21] Appl. No.: 861,154

[22] Filed: Mar. 27, 1992

Related U.S. Application Data

[63] Continuation of Ser. No. 231,078, Aug. 11, 1988, abandoned.

[51] Int. Cl.$^5$ .............................................. A61L 2/00
[52] U.S. Cl. ..................................... 422/295; 34/10; 34/32; 34/57 A; 34/78; 422/307; 432/15; 432/58
[58] Field of Search .................. 422/295, 307; 432/15, 432/58; 34/10, 57 A, 32, 78

[56] References Cited

U.S. PATENT DOCUMENTS

| | | | |
|---|---|---|---|
| 2,552,243 | 5/1951 | Wheeler | 34/2 |
| 3,341,280 | 9/1967 | Eolkin | 422/295 |
| 4,215,151 | 7/1980 | Rios et al. | 432/58 |
| 4,564,965 | 1/1986 | Goodwin | 5/453 |
| 4,615,867 | 10/1986 | Heckman | 432/58 |
| 4,910,880 | 3/1990 | Cole | 432/58 |

FOREIGN PATENT DOCUMENTS 1642087  5/1971  Fed. Rep. of Germany .

Primary Examiner—Peter Chin
Attorney, Agent, or Firm—Dority & Manning

[57] ABSTRACT

An apparatus and method for decontaminating contaminated microspheres of a patient support system employing a fluidizing medium to fluidize the microspheres to provide support for the patient, includes a tank for containing the microspheres. The tank includes a diffuser mounted inside the tank to form a plenum in the bottom of the tank. A rigid shell surrounds heat-insulating material around the outside of the tank. A recirculation channel is defined in the shell. A cover seals the tank. An air heater member and a gas blower provide hot air to fluidize the microspheres inside the tank. A valve permits a heating mode of operation, a cooling mode of operation, and a holding temperature mode of operation. The valve is switched between modes by action of a solenoid or a motor. A temperature probe monitors the temperature inside of the tank. A control circuit controls the air heater, the valve, and the gas blower according to a predetermined timed sequence of actuation. The monitored temperatures are recorded to provide a hard record of same.

The method includes sieving the contaminated microspheres before placing them into the container and fluidizing them with heated air until a predetermined temperature is maintained for a predetermined time. The heated air is recirculated. The decontaminated microspheres are cooled by introducing ambient air into the tank and expelling the hot air from the tank. The heating of the gas is discontinued when the holding temperature is attained and resumed when the temperature falls below the holding temperature.

42 Claims, 8 Drawing Sheets

APPARATUS AND METHOD FOR DECONTAMINATION OF MICROSPHERES USED IN A FLUIDIZED PATIENT SUPPORT SYSTEM

This is a continuation of application Ser. No. 07/231,078, filed Aug. 11, 1988, which was abandoned upon the filing hereof.

BACKGROUND OF THE INVENTION

The present invention relates to an apparatus and method for decontaminating the microspheres used to fluidize a fluidized patient support system.

An improved fluidizable patient support system such as disclosed in U.S. Pat. No. 4,564,965 to Goodwin (hereafter referred to as the Goodwin bed), which is hereby incorporated herein by reference, includes a tank for containing a mass of granular material, preferably ceramic spheres, also referred to as microspheres or beads. These beads have diameters on the order of 50 to 150 microns ($10^{-6}$ meters). A perforated plate provides a false bottom for the tank and together with the bottom and sides of the tank define a plenum. A diffuser board, which is permeable to the flow of air but not to the beads, rests atop the perforated plate and isolates the beads from the plenum. A flexible sheet is removably secured around the upper edges of the tank, and the sheet is permeable to air and liquid but not to passage of the beads therethrough.

When the Goodwin bed is in use, body fluids of the patient and other contaminants pass through the sheet and contaminate the beads. The contaminants cause beads to aggregate into clumps and thereby lessen the efficiency of the fluidization process of the bed. In addition, the contaminants present problems of sanitation and the increased risk of infection with diseases.

The beads periodically must be decontaminated. One method of decontamination requires removing the beads from the Goodwin tank and passing the beads through a sieve to remove the clumps of contaminated material and aggregations of beads from the mass of individual beads. An elongated immersion heater is inserted into the Goodwin tank, and the sieved beads are returned to the tank. The mass of beads is fluidized by the passage of ambient air therethrough, and the immersion heater is operated to heat the beads to a temperature of 55° C. The beads are continuously fluidized and maintained at a temperature no less than 55° C. for 24 hours.

The above method using the Goodwin bed was modified by running the immersion heater at higher temperatures for shorter periods of time. For example, only 12 hours was required if the beads were maintained at a temperature no less than 65° C., 8 hours for a temperature no less than 70° C., 4 hours for a temperature no less than 75° C., 4 hours for a temperature no less than 80° C., 2 hours for a temperature no less than 85° C., and 1 hour for a temperature no less than 90° C.

The use of the above described apparatus is not without its problems. For example, the beads are poor conductors of heat, and those in the vicinity of the immersion heater become too hot and fuse together. Accordingly, the attainment of the higher temperatures necessary for reducing the time required for complete decontamination, exacerbates the bead fusion problems. The fused beads render the fluidization process less efficient and impair the heat distribution efficiency of the decontamination process. These inefficiencies require lengthening the duration of the decontamination process and reduce the advantage of running the immersion heater at higher temperatures.

In addition, maintaining the higher temperatures with the immersion heater often proved difficult or impossible. Significant heat losses are inherent in the Goodwin tank. Attaining the decontamination temperatures and maintaining them over the specified time periods required large energy expenditures and constant monitoring by service personnel. This was a particular problem during winter in many of the service centers performing the decontamination method situated in colder climates and in those service centers which were not well heated.

After the heat treatment portion of the decontamination process is completed, the beads must be allowed to cool to about 40° C. before they can be handled. Cooling the beads takes a significant amount of time. This is especially true when the higher temperatures are attained during the heat treatment and even when the lower temperature heat treatment is carried out during summer months at service centers located in warmer climates. Since the decontamination units are occupied while the beads are cooling, the cooling phase prevents other lots of beads from being decontaminated and reduces the overall efficiency of the service center performing the decontamination process.

Furthermore, the technicians operating the Goodwin bed apparatus sometimes came into contact with the beads being decontaminated due to leakage of beads from the beds into the external environment. Constant monitoring by personnel continued to be required to ensure that at no time during the decontamination period does the temperature fall below the required minimum.

OBJECTS AND SUMMARY OF THE INVENTION

It is a principal object of the present invention to provide an improved apparatus and method for decontaminating the beads used in fluidizable patient support systems.

It is also an object of the present invention to provide an apparatus and method for decontaminating beads of a fluidizable patient support system, wherein the apparatus and method requires less monitoring by operating personnel.

Another object of the present invention is to provide an apparatus and method for decontaminating beads of a fluidizable patient support system, wherein the apparatus and method have improved safety features for operating personnel.

A further object of the present invention is to provide an apparatus and method for decontaminating beads of a fluidizable patient support system, wherein the operating personnel are shielded from physical contact with the contaminated beads.

Yet another object of the present invention is to provide an apparatus and method for decontaminating the beads of a fluidizable patient support system, wherein the damage to the beads during the decontamination process is reduced or eliminated.

Still another object of the present invention is to provide an apparatus and method for decontaminating the beads of a fluidizable patient support system, wherein the efficiency of the apparatus and method is enhanced over prior apparatus and methods.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the apparatus for decontaminating contaminated microspheres of a patient support system employing a fluidizing medium to fluidize the microspheres to provide support for the patient comprises means for containing the microspheres during decontamination of them. The containing means has a first opening therethrough to permit loading of the microspheres into the containing means. The containing means further includes a bottom and a second opening through which air is directed to fluidize the microspheres during decontamination of the microspheres. The second opening preferably is disposed generally in the bottom of the containing means. The apparatus further includes means for separating the bottom of the containing means from the microspheres and for permitting diffusion of a fluidizing medium, such as air, therethrough for fluidizing the microspheres. The separating means is disposed generally between the first and second openings of the containing means to separate these openings from each other. The apparatus further includes means for supporting the containing means. In addition, the apparatus includes means for heat-insulating the containing means. The apparatus also includes means for shielding the operating personnel from physical contact with the outside facing surfaces of the containing means and of the heat-insulating means. The apparatus further includes means for supplying a fluidizing medium, such as gas, through the second opening of the containing means. This fluidizing medium supplying means has an inlet for receiving the fluidizing medium therethrough and has an outlet communicating with the second opening of the containing means. The apparatus also includes means for heating the fluidizing medium prior to passage of the fluidizing medium through the second opening of the containing means. The apparatus also includes means for recirculating the fluidizing medium to the supplying means after the fluidizing medium passes through the microspheres held in the containing means. The recirculating means has an outlet. In addition, the apparatus includes means for preventing the microspheres from being recirculated along with the fluidizing medium. The apparatus further includes means for valving the fluidizing medium for at least two alternative modes of operation. During a first mode of operation, sometimes referred to as the heating mode, the heated fluidized medium is recirculated to conserve heat energy. During a second mode of operation, sometimes known as the cooling mode, the heated fluidizing medium is expelled from the decontamination apparatus, and an alternative source of fluidizing medium, such as room temperature air or refrigerated air, is supplied to the fluidizing medium supplying means. In addition, the apparatus includes means for monitoring the temperature inside the containing means. The apparatus further includes means for controlling actuation of the heating means, the valving means, and the fluidizing medium supplying means according to a predetermined sequence and according to monitored performance of the apparatus. The control means is connected to the temperature monitoring means.

An example of the containing means includes a tank which has a bottom, two opposite sides, two opposite ends, and wherein the sides and ends define a first opening of the tank.

An example of the separating means comprises a diffuser board disposed in the containing means above the bottom of the containing means to form a plenum between the diffuser board and the bottom of the containing means.

An example of the supporting means includes a stand having at least one base member for resting on the floor. The stand receives the tank and supports the tank at a predetermined height above the base member.

An example of the heat-insulating means for the containing means includes a heat-insulation blanket surrounding the containing means and being attached thereto. The heat-insulating means also can include a heat-insulation board disposed between the bottom of the containing means and the supporting means so as to thermally isolate the containing means bottom from the supporting means.

An example of the shielding means includes a rigid shell formed of heat-insulating material. The shell preferably is configured to cover the containing means and the insulating means surrounding the containing means. The shell defines a shell opening at the top thereof to expose the first opening of the containing means. The shielding means can also include a cover which is heat-insulated and configured to cover the shell opening. The shielding means also can include at least one hinge attached to the cover and to the shell to facilitate opening and closing the cover. Preferably, more than one hinge is provided, and the shell and shell cover are preferably molded fiberglass structures.

An example of the recirculating means includes a gas recirculation channel defined in the shell which forms the shielding means. The channel communicates between the first opening of the containing means and the fluidizing medium supplying means.

The personnel who operate the decontamination apparatus need to be protected against physical contact with the contaminated microspheres and the heated microspheres. The decontamination apparatus also can include means for sealing the cover against the shell to prevent leakage of the microspheres during the operation of the apparatus to decontaminate the contaminated microspheres. An example of the sealing means can include a flexible gasket disposed on the periphery of the shell cover so as to rest atop the shell around the shell opening when the cover is closed against the shell. The sealing means also can include a spring-biased hooking device for pressing the cover against the shell gasket around the edge of the cover that carries the hinges. The sealing means also can include at least two J-shaped, spring-actuated clamping members that press the cover in the vicinity of the edge opposite the edge carrying the hinges. The clamping members press the cover against the shell, or the gasket disposed on the shell if present, near the shell opening.

An example of the fluidizing medium supplying means includes a gas blower having a gas inlet for receiving air therethrough and having a gas outlet connected in communication with the second opening of the containing means.

An example of the heating means comprises an air heater member that has an outlet for heated air. The outlet is connected to the second opening of the containing means. The air heater member also has an air inlet for receiving the air to be heated.

An example of the means for preventing microspheres from being recirculated along with the fluidizing medium, comprises a filter disposed in the recirculation channel in a manner that prevents the microspheres from moving through the air recirculation channel.

An example of the valving means comprises an air valve having at least four air flow access conduits. A first one of the conduits is dedicated to receive ambient air. A second conduit is dedicated for expelling air from the containing means to the ambient atmosphere. The first conduit acts as an inlet, and the second conduit acts as an exhaust. A third conduit communicates with the gas inlet of the fluidizing medium supplying means. A fourth conduit communicates with the outlet of the recirculating means. The valving means can also include means for switching the valve between a heating mode of operation and a cooling mode of operation. The heating mode of operation includes configuring the valve to connect the fourth air flow access conduit to the third air flow access conduit. The cooling mode includes configuring the valve to connect the first conduit to the third conduit and also connect the fourth conduit to the second conduit.

An example of the valve switching means can include a valve passage having an opening at opposite ends thereof, a pair of cover plates, a pair of connecting members, a pair of electrically actuatable solenoids, and means for biasing the cover plate. One of the cover plates can be disposed near each end of the valve passage. Each connecting member has one end connected to one of the cover plates. Each solenoid is connected to an opposite end of one of the connecting members. The biasing means is structured to bias each cover plate against the respective nearby end of the valve passage to prevent flow of the gas therethrough. An example of the biasing means for each cover plate includes a spring attached at one end to each cover plate. Actuation of each solenoid causes each respective cover plate to move away from and thereby uncover each respective nearby end of the valve passage and cover each nearby first air flow access conduit and second air flow access conduit and thus change the gas flow configuration of the valve.

An example of the actuation control means includes an electrical control circuit. The electrical control circuit can include a timer and electrical switching means for electrically permitting the timer to control the supply of electrical power to each of the heating means, the valving means, and the fluidizing medium supplying means. An example of the electrical switching means can include at least one electrical relay for each of the heating means, the valving means, and the fluidizing medium supplying means. An example of the timer can include a programmable electronic microprocessor unit.

An example of the temperature monitoring means can include a temperature probe disposed to project inside the containing means and immersed in the fluidized microspheres.

The decontamination apparatus also can include means for screening the microspheres before they enter the containing means. An example of the screening means includes a sieving screen having openings therethrough that are sized to prohibit passage of aggregations of microspheres through the sieving screen openings while allowing passage of individual microspheres. It also includes a plurality of sieve support means mounted to the interior of the containing means for supporting the rigid frame on which the sieving screen is mounted. An example of the sieve support means can include a plurality of eyelet bolts threaded on one end and screwed into opposite sides of the containing means.

The decontamination apparatus also can include a plurality of protective bumpers that are mounted around the outside-facing periphery of the shell. The bumpers protect the decontamination device from collisions as mobile equipment at the service center housing the decontamination apparatus is moved from place to place.

To achieve the objects of the invention and in accordance with the purpose of the invention as embodied and broadly described herein, the method for decontaminating contaminated microspheres of a patient support system employing a fluidizing medium to fluidize the microspheres to provide support for the patient includes the following steps. The contaminated microspheres are sieved to remove clumps of microspheres larger than a predetermined size, which depends upon the opening size of the sieve. The microspheres passing through the sieve are introduced into a container so as to isolate them from physical contact with the environment during the decontamination method. A fluidizing medium, such as air, is heated. The microspheres are fluidized by providing the heated fluidizing medium under pressure into the bottom of the container that holds the microspheres. The heated fluidizing medium is continuously provided to fluidize the microspheres and heat and maintain their temperature at a predetermined temperature for a predetermined period of time. The predetermined temperature is greater than 55° C. The predetermined period of time varies according to the predetermined temperature. The heated fluidizing medium is continuously recirculated into and out of the container to conserve heat energy during the heat decontamination of the microspheres. After the predetermined period of time elapses, the microspheres are cooled. Cooling is accomplished by introducing ambient air into the container and expelling the heated fluidizing medium from the container to the atmosphere. The decontamination process is documented by continuously monitoring the temperature inside the container during the decontamination of the beads and recording this monitored temperature.

The decontamination method also can include cooling the microspheres until they attain a minimum holding temperature. The holding temperature is selected so as to prevent the accumulation of moisture in the microspheres that might occur by condensation of the moisture from the ambient air that is used to cool the microspheres. Thus, the minimum holding temperature is preselected depending upon the anticipated ambient atmospheric conditions, such as pressure, humidity, and temperature.

The method of decontamination also can include discontinuing the heating of the fluidizing medium until the holding temperature is attained and resuming the heating of the fluidizing medium to maintain the holding temperature. Thus, the temperature of the microspheres can be monitored and the heat turned on and off so as to keep the temperature of the microspheres as close as possible to the holding temperature.

The preferred combinations of predetermined temperatures and predetermined time periods include the following pairings:

(1) 55° C. and 24 hours;
(2) 65° C. and 12 hours;
(3) 70° C. and 8 hours;
(4) 75° C. and 4 hours;
(5) 80° C. and 4 hours;
(6) 85° C. and 2 hours; and
(7) 90° C. and 1 hour.

The accompanying drawings, which are incorporated in and constitute a part of this specification, illustrate embodiments of the invention and together with the description serve to explain the principles of the invention.

DESCRIPTION OF THE PREFERRED EMBODIMENTS

Reference now will be made in detail to the present preferred embodiments of the invention, examples of which are illustrated in the accompanying drawings. A preferred embodiment of the decontamination apparatus is indicated generally in FIG. 1 by the designating numeral 20.

Figure 1:
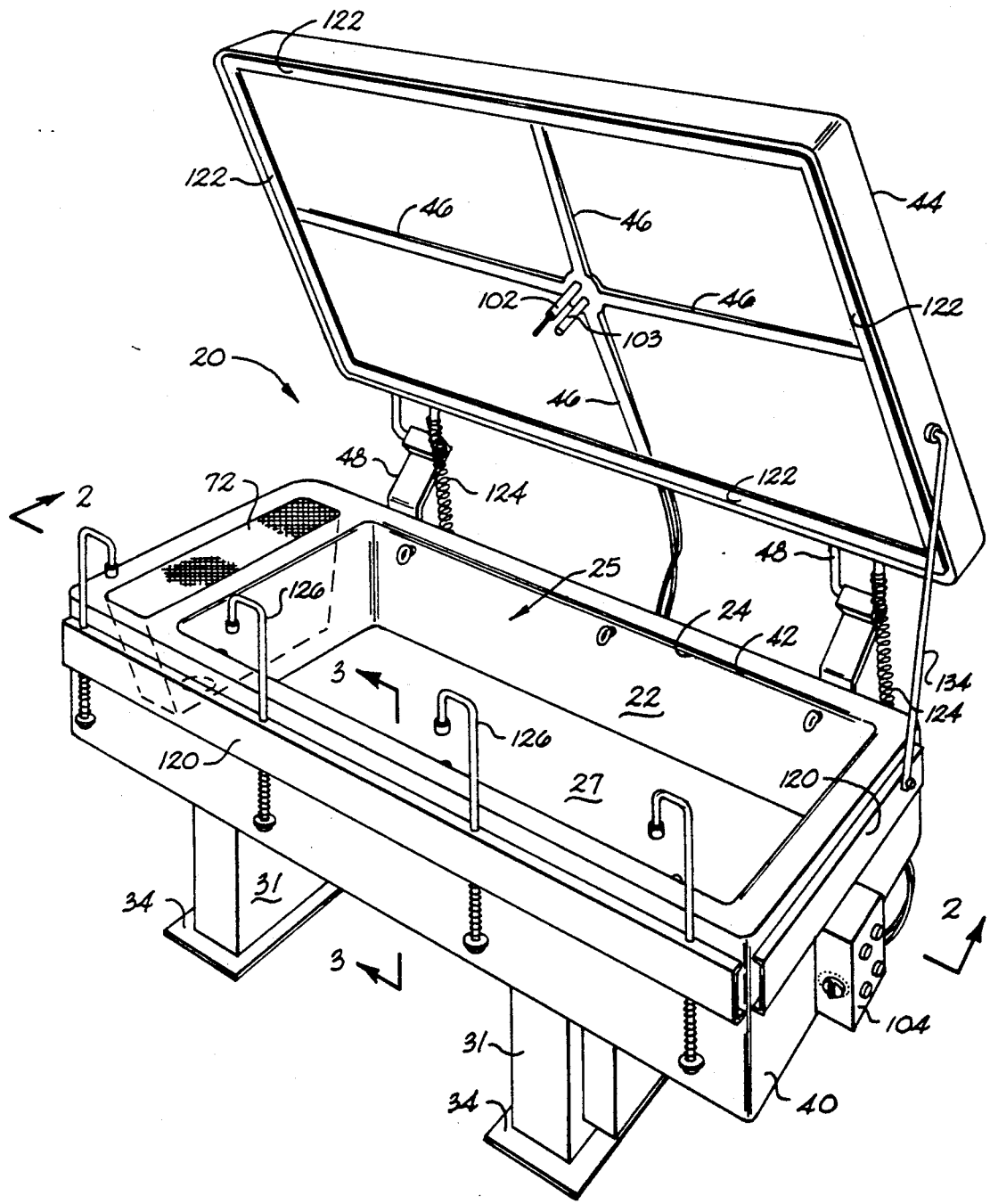
FIG. 1 is a perspective view of an embodiment of the apparatus of the present invention.
Figure 2:
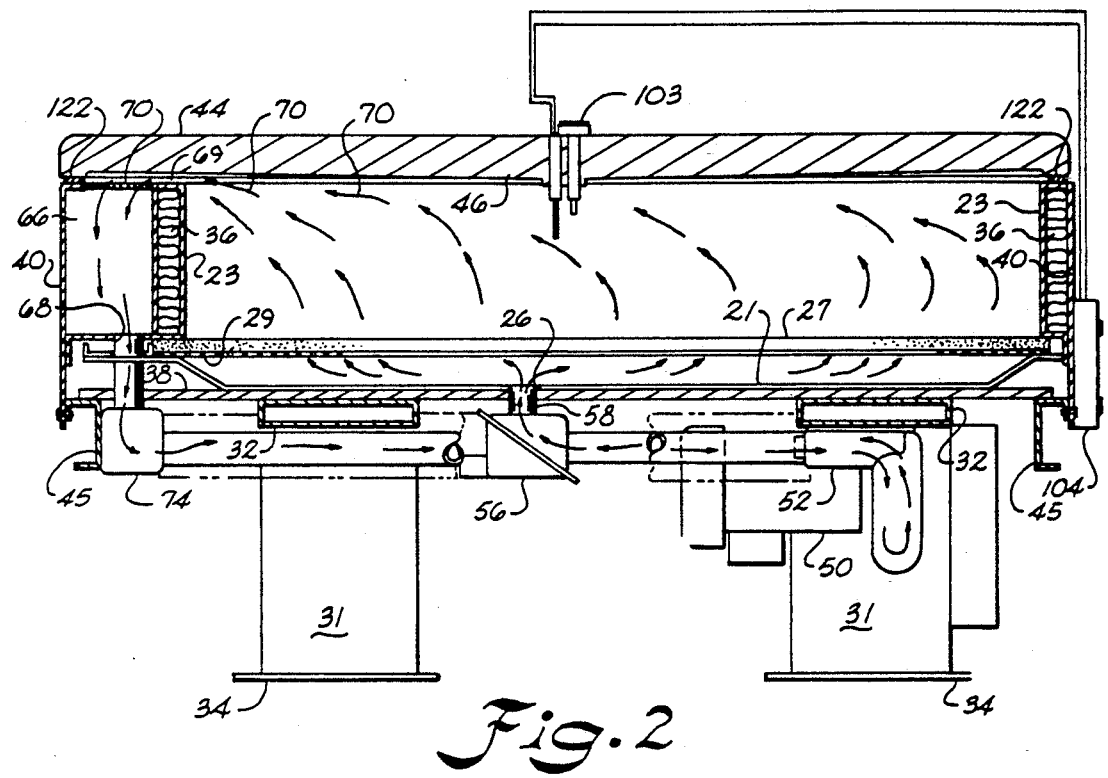
FIG. 2 is a cross-sectional view taken along the lines 2—2 of FIG. 1 and having certain components shown in phantom and a plurality of arrows showing the direction of air flow.
Figure 3:
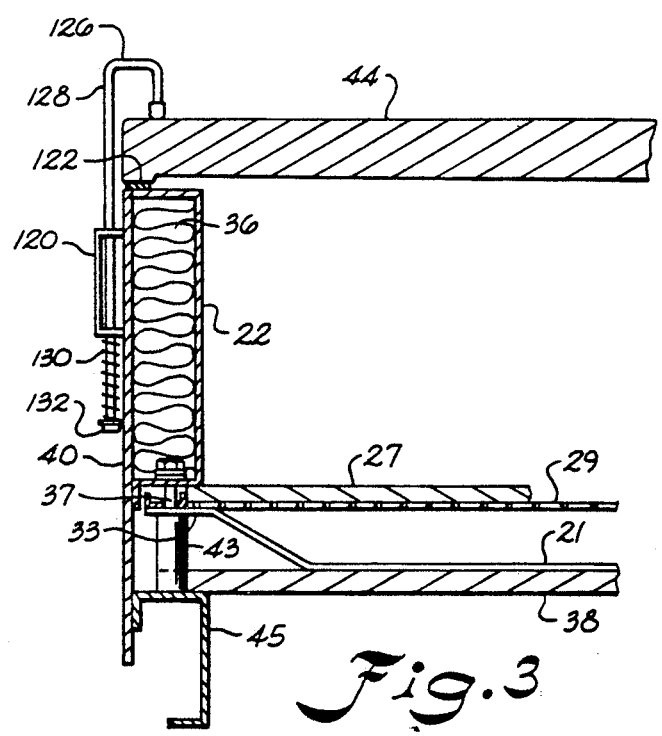
FIG. 3 is a partial cross-sectional view taken along the lines of 3—3 of FIG. 1.
Figure 8:
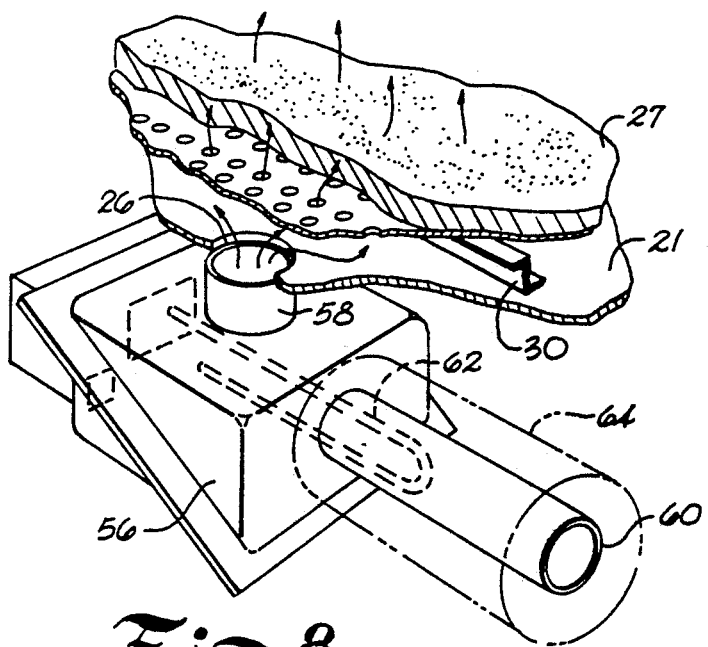
FIG. 8 is a perspective view of components of the apparatus of the present invention with certain structure shown in phantom and arrows showing the direction of air flow.

A preferred embodiment of the apparatus for decontaminating contaminated microspheres of a patient support system employing a fluidizing medium to fluidize the microspheres to provide support for the patient comprises means for containing the microspheres during decontamination of the microspheres. As embodied herein and shown for example in FIGS. 1 and 2, the containing means preferably includes a tank which is indicated generally in FIG. 1 by the designating numeral 25. As shown in FIGS. 2 and 3 for example, tank 25 has a bottom 21. As shown in FIGS. 1 and 3 for example, tank 25 has a pair of opposite sides 22. As shown in FIG. 2 for example, tank 25 has a pair of opposite ends 23. As shown for example in FIG. 1, the free edges of sides 22 and ends 23 are joined to define a first opening 24 of tank 25. As shown in FIGS. 2 and 8 for example, a second opening 26 is defined in bottom 21 of tank 25.

In accordance with the present invention, means are provided for separating the bottom of the containing means from the microspheres and for permitting diffusion of a fluidizing medium, such as air, through the separating means in order to fluidize the microspheres. The separating means is disposed generally between the first and second openings of the containing means to separate these openings from each other. As embodied herein and shown for example in FIGS. 1, 2, 3, 4, and 8, the separating means preferably comprises a diffuser board 27. Preferably, diffuser board 27 is formed of a composite of pressed fibers. Diffuser board 27 also can be rendered hydrophobic by the application of a coating of a known resin material, such as that sold under the SCOTCH-GARD trademark and comprising a fluoroaliphatic resin and 1, 1, 1 - trichlorethane carrier. The resin is preferably sprayed onto diffuser board 27 and thus does not form a continuous layer of resin. Only the side of diffuser board 27 facing the microspheres inside tank 25 need be sprayed with the resin. The resin coating reduces the amount of fiber which separates from the board and mixes with the microspheres during the fluidizing process. Such separated fibers tend to become reservoirs of contaminants. The hydrophobic nature of the resin applied to the diffuser board 27 also reduces the likelihood that the diffuser board will become imbued with liquid contaminants from the contaminated microspheres.

Figure 4:
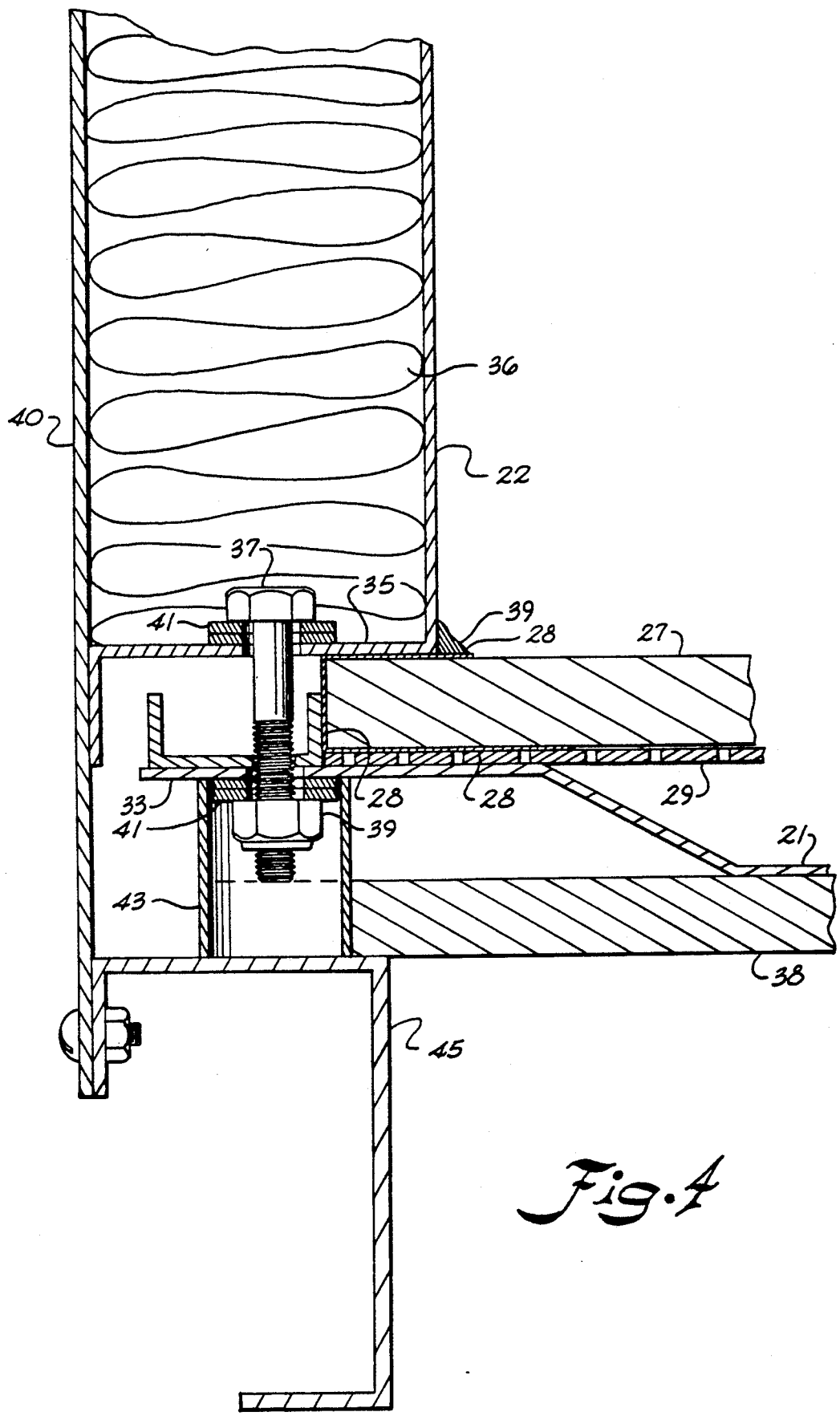
FIG. 4 is another partial cross-sectional view expanded and similar to the view shown in FIG. 3.

Diffuser board 27 is permeable to air but impermeable to the passage of microspheres therethrough. As shown in FIG. 4 for example, the edges of diffuser board 27 are wrapped in duct tape 28 or any other material which is impermeable to passage of air therethrough, so that gas, such as air, cannot be diffused through the edges of diffuser board 27. As shown in FIGS. 3 and 4 for example, diffuser board 27 preferably is held between peripheral flanges 33 of tank bottom 21 and lower flanges 35 of sides 22 and ends 23 of tank 25. As shown in FIG. 4 for example, a plurality of partially threaded bolts 37 join lower flanges 35 of tank sides 22, the edge of diffuser board 27 surrounded by duct tape 28, the edge of perforated plate 29, and peripheral flanges 33 of tank bottom 21. The base of a flange having a generally U-shaped transverse cross-section is secured atop peripheral flange 33. As shown in FIG. 4 for example, the inside leg of the U-shaped flange provides a stop against which the respective edges of diffuser board 27 and perforated plate 29 rest to facilitate assembly. Bolts 37 are passed through openings in peripheral flange 33 and U-shaped flange. Bolt 37 is screwed into a threaded nut 39, and one or more washers 41 can be used as needed for a secure attachment. Each bolt 37 is provided with a cylindrical sleeve 43 surrounding same as shown for example in FIG. 4. The same attachment mechanism is provided for tank ends 23. In addition, a bead 39 of room temperature vulcanizing (RTV) compound, such as silicone rubber sealant which hardens at room temperature, is applied inside tank 25 where the lower flanges of tank sides 22 and ends 23 meet diffuser board 27.

As shown in FIGS. 2, 3, and 4, a perforated support plate 29 provides structural support to bolster the physical integrity of diffuser board 27. A complete load of microspheres can weigh 1,000 pounds or more, and the initial dumping of the microspheres into tank 25 can place considerable stress on diffuser board 27. Support plate 29 is preferably made of metal or another rigid material. Perforated plate 29 has holes therethrough over the greater portion of its area to permit air to pass through perforated plate 29 and through diffuser board 27.

A plurality of support ridges 30 can be disposed between tank bottom 21 and support plate 29 to provide further support for diffuser board 27. Support ridges 30 preferably comprise Z-bars which extend lengthwise along the surface of tank bottom 21. Preferably three support ridges 30 are provided, and part of one can be seen in FIG. 8 for example.

In accordance with the present invention, means are provided for supporting the containing means. As embodied herein and shown for example in FIGS. 1 and 9, the supporting means for the containing means includes a stand comprising a pair of support stanchions 31. Each stanchion 31 supports a bed support 32 shown for example in FIG. 2, and side support members 45 shown for example in FIGS. 2-4. Each stanchion 31 has a base member 34 for resting on the floor. The weight of tank 25, including a full load of contaminated microspheres, is supported by stanchions 31 via side support members 45 and a plurality of support sleeves 43. As shown for example in FIG. 4, each support sleeve 43 preferably comprises a cylindrical metal pipe section which supports peripheral flanges 33 of tank bottom 21 at one end of support sleeve 43. The opposite end of support sleeve 43 rests upon a horizontally disposed flange portion of a side support member 45. Bed support 32 also is attached to stanchion 31. Thus, side support members 45, support sleeves 43, and bed support 32 cooperate to receive tank bottom 21 and together with stanchion 31 support tank bottom 21 at a predetermined height above base member 34. Preferably, a plurality of support sleeves 43 is provided on each side of the decontamination unit. Four (4) support sleeves on each side have been found to provide adequate structural support. The stand, including bed support 32, side support members 45, support sleeves 43 and stanchion 31, is preferably formed of a sturdy metal construction capable of withstanding the significant weight of the microspheres and the components of the decontamination apparatus.

In further accordance with the present invention, means are provided for heat-insulating the containing means. As embodied herein and shown for example in FIGS. 2, 3 and 4, the means for heat-insulating the containing means includes a heat-insulation blanket 36 surrounding tank sides 22 and tank ends 23. Blanket 36 preferably is formed of fiberglass heat-insulating material. As shown in FIGS. 2 and 3 for example, the heat-insulating means further includes a heat-insulation board 38 preferably disposed between the bottom of the containing means and the supporting surface of the supporting means so as to thermally isolate the containing means bottom from the supporting means. This is especially important when both the containing means and the supporting means are formed of heat-conducting material such as metal. As shown in FIG. 2 for example, heat-insulation board 38 rests atop bed support 32, and tank bottom 21 is disposed above heat insulation board 38 so that tank bottom 21 is thermally isolated from bed support 32. Heat-insulation board 38 preferably is formed of fiberglass or similar materials capable of minimizing heat conduction therethrough. As shown for example in FIG. 4, heat insulation board 38 has cut out portions for receiving each support sleeve 43 surrounding each bolt 37 and nut 39.

The structural integrity of heat insulation board 38 cannot support the weight of the tank filled with microspheres. This weight is supported by support sleeves 43. As shown in particular in FIG. 4 for example, support sleeves 43 constitute the only metal-to-metal contact between tank bottom 21 and any portion of the supporting means for the containing means, which in this case comprises the horizontally extending portion of side support member 45. Since preferably only eight support sleeves 43 are employed, this constitutes a very small surface area through which conductive heat transfer can occur between tank 25 and side support member 45. Thus, heat transfer loses from conductive heat transfer is minimized without sacrificing the structural integrity of the decontamination unit.

The containing means is subject to high temperatures during the decontamination process, and it is desirable to protect the operating personnel from touching hot surfaces. In yet further accordance with the present invention, means are provided for shielding the personnel operating the decontamination unit from direct physical contact with the outside facing surfaces of the containing means and/or heat-insulating means. As embodied herein and shown for example in FIGS. 1-3, the means for shielding the operating personnel includes a rigid shell 40 which preferably is formed of molded fiberglass. Rigid shell 40 also can be made of other materials, such as aluminum. Shell 40 preferably is configured to cover the containing means and the heat-insulating means surrounding the containing means. As shown in FIG. 1 for example, shell 40 defines a shell opening 42 to expose first tank opening 24. As embodied herein and shown in FIGS. 1-3 for example, the shielding means further comprises a shell cover 44, which preferably is heat-insulated and configured to cover shell opening 42. Cover 44 can be formed of molded fiberglass or aluminum and can be configured as shown in FIGS. 1 and 2 with one or more reinforcing structures 46. Reinforcing structures 46 prevent cover 44 from warping under the stresses associated with the high temperatures attained within tank 25 during the decontamination process. As shown for example in FIG. 1, the shielding means as embodied herein can further include at least one hinge 48 attached to cover 44 and shell 40 to facilitate opening and closing cover 44. Preferably at least two hinges 48 are provided. Hinges 48 preferably are formed of metal or another sturdy rigid substance.

Figure 5:
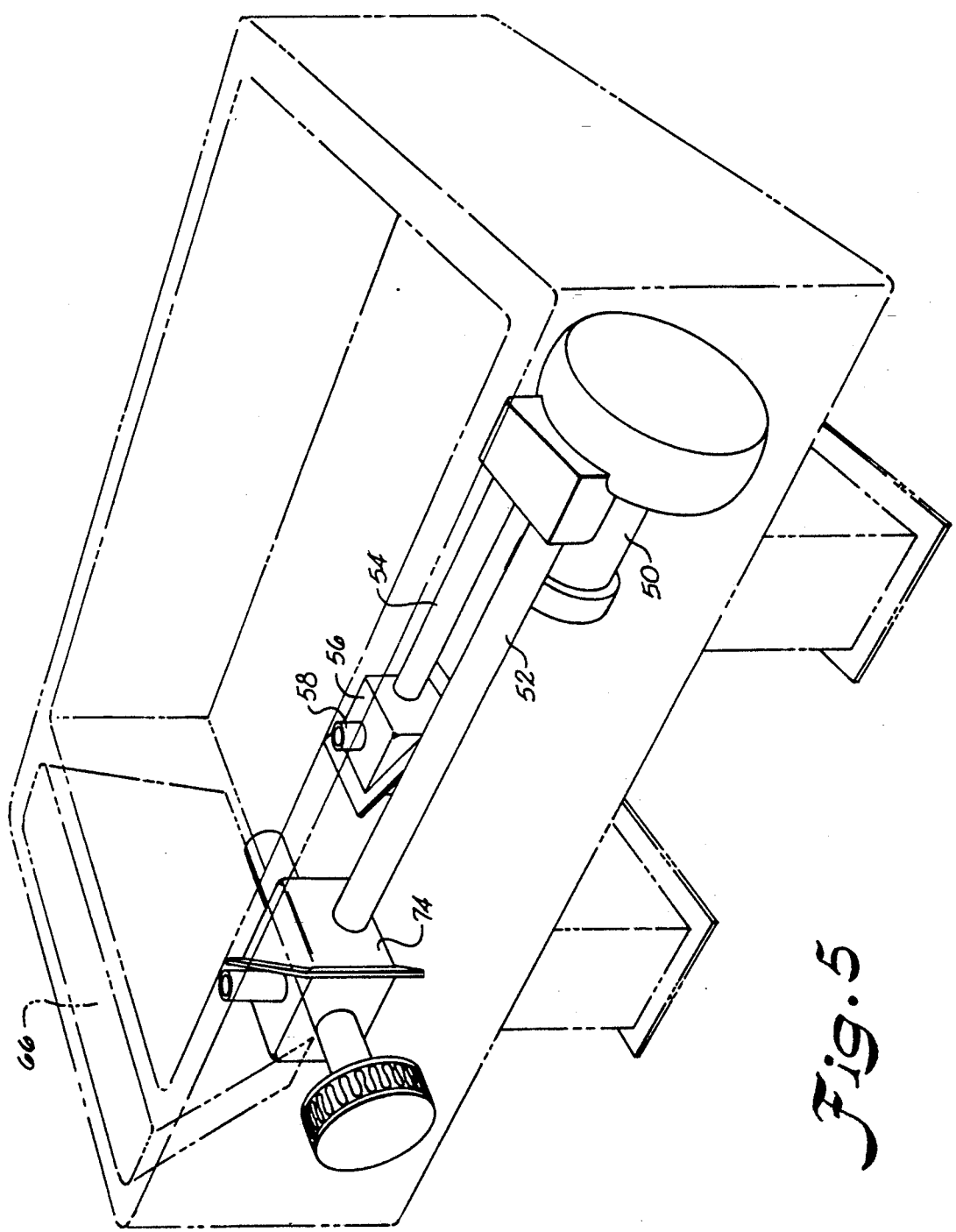
FIG. 5 is a perspective view of components of the apparatus of the present invention with certain structures shown in phantom.

In accordance with the present invention, means are provided for supplying a fluidizing medium through the second opening of the containing means. The fluidizing medium supplying means has an inlet for receiving the fluidizing medium, such as a gas like ambient air, therethrough and has an outlet communicating with the second opening of the containing means. The fluidizing medium is supplied to the containing means through the second opening. As embodied herein and shown in FIGS. 2 and 5 for example, a preferred embodiment of the fluidizing medium supplying means includes a gas blower 50, which preferably comprises an air compressor. A one horsepower Rotron electric blower is one example of a suitable gas blower. Gas blower 50 has a gas inlet 52 for receiving air. Gas blower 50 also includes a gas outlet 54 which is connected in communication with second opening 26 of tank bottom 21 of tank 25.

In further accordance with the present invention, means are provided for heating the fluidizing medium prior to passage of the fluidizing medium through the second opening of the containing means and fluidizing of the microspheres with the fluidizing medium. As embodied herein and shown for example in FIGS. 2, 5, and 8, the heating means preferably includes an air heater member 56, which has an outlet 58 connected to second opening 26 of tank 25. As shown for example in FIG. 8, air heater member 56 also has an air inlet 60 for receiving the air to be heated by heater member 56. Air heater member 56 also includes an electric heating element 62, which is shown in phantom in FIG. 8 along with a heat insulation sheath 64, which is formed of heat-insulating material and surrounds air inlet 60. One example of heater element 62 is a four kilowatt electrical resistance heater, which operates from a 20 ampere 240 volt alternating current circuit.

In accordance with the present invention, means are provided for circulating the fluidizing medium to the fluidizing medium supply means after the fluidizing medium passes through the containing means and fluidizes the microspheres. This so-called recirculating means has an outlet. As embodied herein and shown for example in FIGS. 2 and 5, the recirculating means preferably comprises a gas recirculation channel 66 defined at one end of protective shell 40. Recirculation channel 66 has an outlet 68 shown in FIGS. 2 and 6 for example. The arrows designated 70 in FIG. 2 show the path of gas from tank 25 to recirculation channel 66.

As shown in FIG. 2, the end 23 of tank 25 which defines one side of the internal side wall of recirculation channel 66 cooperates with cover 44 to define a narrow slot 69 through which the fluidizing medium to be recirculated passes before reaching filter 70. Narrow slot 69 therefore acts as a constriction in the flow of fluidizing medium, and this restriction tends to reduce the number of microspheres which reach filter 70. This is accomplished by forcing the fluidizing medium to flow horizontally to gain entrance through narrow slot 69. The turning of the microspheres to flow horizontally permits gravity to remove microspheres from the stream of fluidizing medium. Thus, the narrow slot comprises means for constricting the flow of fluidizing medium during recirculation of same.

In accordance with the present invention, means are provided for preventing the microspheres from being recirculated together with the fluidizing medium. As embodied herein and shown for example in FIGS. 1 and 9, the means for preventing the microspheres from being recirculated together with the fluidizing medium includes a filter 72 which is disposed generally across one end of recirculation channel 66 near first opening 24 of tank 25. Filter 72 preferably comprises a fine mesh screen which prevents passage of microspheres, but not air, therethrough.

Figure 6:
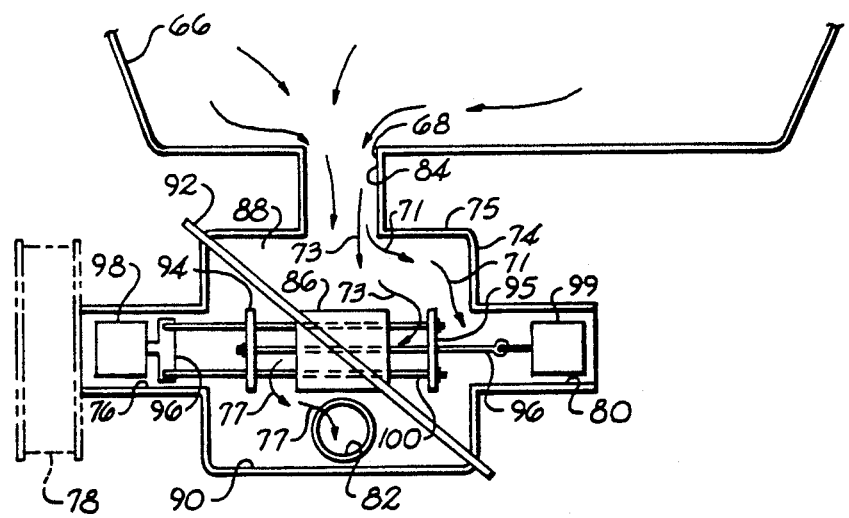
FIG. 6 is a schematic diagram of components of the apparatus of the present invention.

In still further accordance with the present invention, means are provided for valving the fluidizing medium for at least two alternative modes of operation. In a first mode of operation, sometimes referred to as the heating mode, heated fluidizing medium is received from the recirculating means and routed to the fluidizing medium supplying means. During a second alternative mode of operation, sometimes referred to as the cooling mode, the heated fluidizing medium passing through recirculation outlet 68 is expelled from the decontamination apparatus while an alternative source of fluidizing medium, such as ambient air, is routed to the fluidizing medium supplying means. As embodied herein and shown for example in FIGS. 2, 5, and 6, the valving means preferably includes a valve indicated generally by the designating numeral 74 in FIGS. 5 and 6. As shown in FIG. 6 for example, valve 74 includes a housing 75 and a first air flow access conduit 76, which is dedicated for receiving ambient air. First conduit 76 can be attached to an air filter 78 (shown in phantom in FIG. 6) to remove particulate matter from ambient air entering first conduit 76. A second air flow access conduit 80 is dedicated for expelling air from the containing means to the ambient atmosphere. A third air flow access conduit 82 communicates with gas inlet 52 of the fluidizing medium supplying means. A fourth air flow access conduit 84 communicates with recirculation channel outlet 68.

Figure 7:
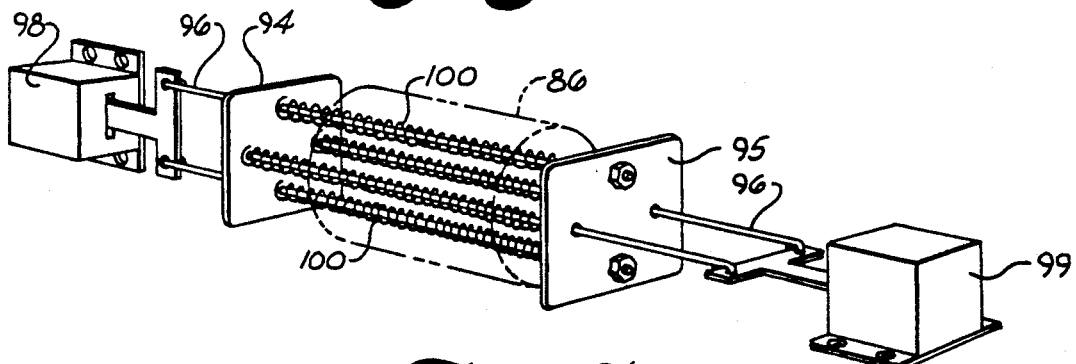
FIG. 7 is a perspective view of components of the apparatus of the present invention with certain structure shown in phantom.

The valving means further comprises means for switching the valve between at least two alternative modes of operation, such as a heating mode of operation and a cooling mode of operation. The heating mode of operation includes configuring the valve to connect fourth air flow access conduit 84 with third air flow access conduit 82. The cooling mode includes configuring the valve to connect first conduit 76 with third conduit 82 and connecting fourth conduit 84 to second conduit 80. One embodiment of the valve switching means shown for example in FIGS. 6 and 7, includes a valve passage 86 (shown in phantom in FIG. 7) which connects two valve chambers 88 and 90 which are separated by a dividing wall 92. As shown in FIGS. 6 and 7 for example, valve passage 86 can be defined by a cylinder having openings at opposite ends thereof. The valve switching means further includes a pair of cover plates 94, 95. One cover plate 94 is disposed near one end of valve passage 86, and the other cover plate 95 is disposed near the opposite end of valve passage 86. The valve switching means further includes a pair of connecting members 96 which are connected at one end to one of cover plates 94, 95. The valve switching means also includes a pair of electrically actuated solenoids 98, 99, each of which is connected to a respective opposite end of one of connecting members 96.

The valve switching means further includes means for biasing each cover plate against its respective nearby end of valve passage 86. As embodied herein and shown for example in FIG. 7, the biasing means for each cover plate 94, 95 comprises at least one spring 100 which has one of its ends attached to one cover plate 94 and the other of its ends attached to the other cover plate 95. Preferably a plurality of springs 100 are attached at different sites on cover plates 94, 95. Springs 100 extend through passage 86. The valve switching means also can include means for biasing each cover plate away from its respective nearby end of the valve passage. As embodied herein and shown for example in FIGS. 6 and 7, the means for biasing each cover plate away from the respective nearby end of the valve passage can include a pair of solenoids 98, 99. One solenoid 98 is connected to one cover plate 94 and the other solenoid 99 is connected to the other cover plate 95. Actuation of each solenoid 98, 99 causes each respective cover plate 94, 95 to move away from and discontinue covering valve passage 86 and to cover each respective nearby end of first conduit 76 or second conduit 80 to prevent flow of gas therethrough and thereby change the gas flow configuration of valve 74.

Operation of valve 74 can be illustrated most easily by reference to FIG. 6. Springs 100 bias cover plate 95 against the open end of valve passage 86 to permit gas flow indicated by arrows designated 71 to travel from recirculation channel 66 through recirculation outlet 68 and fourth air flow access conduit 84 and into second air flow access conduit 80 of valve 74 to exit valve 74 and enter the ambient atmosphere.

The configuration of valve 74 for the heating mode of operation is accomplished as follows. Activation of solenoid 99 against the biasing force of springs 100 to move cover 95 away from passage 86 causes gas flow indicated by arrows designated 73 to travel from recirculation channel 66 through recirculation outlet 68 and fourth air flow access conduit 84 and through valve passage 86. Activation of solenoid 98 to move cover 94 away from the open end of valve passage 86 permits the gas to flow as indicated by the arrows designated 77 to travel through third air flow access conduit 82 into gas inlet 52 (not shown in FIG. 6) and eventually to gas blower 50. Thus, activation of both solenoids 98, 99 against the biasing force of springs 100 to move covers 94, 95 away from passage 86 causes gas flow as indicated by the arrows designated 73 and 77 to travel from recirculation channel 66 to gas inlet 52 of gas blower 50. When gas blower 50 is operating, it imposes a suction on valve chamber 90 through gas inlet 52 and third air flow access conduit 82. This suction draws in fresh air through first air flow access conduit 76 so long as solenoid 98 is not actuated so as to pull cover 94 into a position to block access to first air flow access conduit 76.

Actuation of solenoids 98, 99 to permit respective cover plates 94, 95 to uncover the open ends of valve passage 86 reconfigures valve 74 for a first mode of operation known as the heating mode of operation. As long as covers 94, 95 are disposed away from the open end of valve passage 86 in valve chambers 88, 90, gas entering valve chambers 88, 90 is drawn toward and through third air flow access conduit 82 by the suction applied by operation of gas blower 50. This corresponds to the heating mode of operation wherein the heated fluidizing medium is recirculated from the containing means back to the fluidizing medium supplying means so as to conserve heat energy supplied by the heating means. In the heating mode of operation, solenoids 98, 99 not only move cover plates 94, 95 away from valve passage 86, but also move cover plates 94, 95 to shut off, i.e., block the air flow through, first air flow access conduit 76 and second air flow access conduit 80, respectively. This blockage of first conduit 76 (also known as the air inlet for decontamination unit 20) and second conduit 80 (also known as the exhaust for the decontamination unit) is preferably not an air-tight blockage. However, because of the relative pressure losses associated with gas flow through conduits 76, 80, and 82 and air passage 86, flow entering chamber 88 from conduit 84 flows primarily through passage 86 and conduit 82.

The absence of an air-tight blockage in valve 74 is desired to avoid pressure increases within the decontamination unit during the heating mode of operation. Since the air or other fluidizing medium passing through valve 74 has been filtered to remove microspheres therefrom, the less than air-tight blockage is unlikely to result in the escape of contaminated microspheres.

Deactivation of solenoids 98, 99 to permit respective plates 94, 95 to cover each end of valve passage 86 reconfigures valve 74 for a second mode of operation known as the cooling mode of operation when heater 56 is turned off. In the cooling mode of operation, ambient air is drawn into valve chamber 90 through first air flow access conduit 76 and routed through third air flow access conduit 82 to gas inlet 52 and gas blower 50 for provision through second tank opening 26 to fluidize microspheres inside tank 25. The cooling mode of operation also includes configuring valve 74 so that heated air returning from tank 25 through recirculation channel 66 into valve chamber 88 exits valve 74 through second air flow access conduit 80 to the ambient atmosphere, as shown by the arrows designated 71 in FIG. 6. This is accomplished by covering passage 86 with cover plate 95.

An alternative embodiment of the valve switching means is illustrated schematically for example in FIG. 11 in which the designating numeral "2". has been used as a prefix to the designating numerals used to describe similar structure in the embodiments illustrated in FIGS. 6–8. As shown in FIG. 11 for example, a valve 274 has a first conduit 276 communicating with the ambient atmosphere and a second conduit 280 communicating with a discharge outlet (not shown) for carrying away exhausted fluidizing medium. Valve 274 also includes a third conduit 282 communicating with an embodiment of the fluidizing medium supplying means, such as blower 250, and a fourth conduit 284 communicating with the first opening of tank 225. The valve switching means preferably includes a movable divider 292, which is shown in FIG. 11 as being pivotally mounted at 293. Thus, divider 292 is disposed to move between a first position shown in FIG. 11 with divider 292 indicated in a solid line, and a second position shown in FIG. 11 with divider 292 indicated in a dashed line. The first position of divider 292 allows communication between first conduit 276 and second conduit 280, and thus permits communication between the ambient atmosphere and the discharge outlet. The first position also permits communication between third conduit 282 and fourth conduit 284 and thus allows fluidizing medium coming from the first opening of tank 225 to travel to the inlet of blower 250 for recirculation into the second opening of tank 225. A recirculation conduit 254 is indicated schematically in FIG. 11 to show the connection between the outlet of blower 250 and the second opening of tank 225.

In the second position of divider 292 shown by the dashed line in FIG. 11, communication is allowed between first conduit 276 and third conduit 282. The second position of movable divider 292 also allows communication between second conduit 280 and fourth conduit 284. When movable divider 292 assumes the first position, this corresponds to configuring valve 274 to allow the decontamination unit to operate in the heating mode during which the heated fluidizing medium is recirculated through blower 250 and provided into tank 225 via a recirculation mechanism such as recirculation conduit 254. When divider 292 assumes the second position, this corresponds to configuring valve 274 to permit the decontamination unit to operate in the cooling mode of operation during which heated fluidizing medium is exhausted to the discharge outlet and ambient air or refrigerated air is provided to the inlet of blower 250 and pumped into tank 225.

Figure 11:
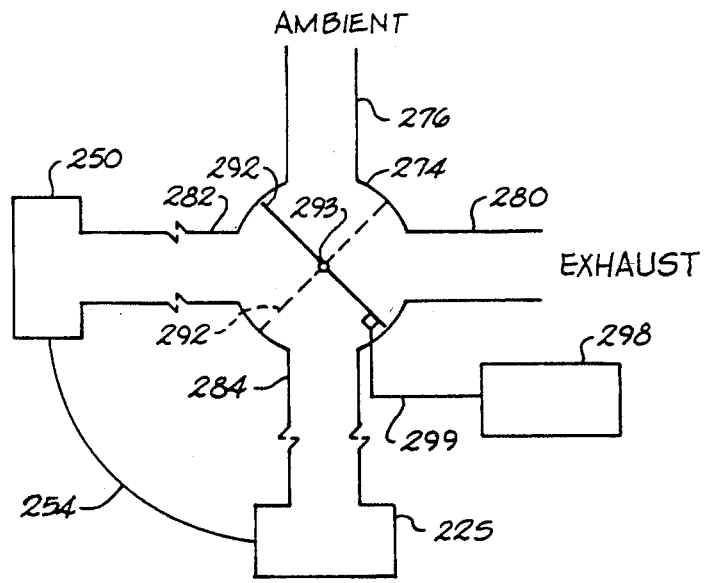
FIG. 11 is a schematic diagram of alternative embodiments of components of an embodiment of the present invention.

The embodiment of the valve switching means illustrated in FIG. 11 further includes means for selectively moving the movable divider between the first position and the second position. As embodied herein and shown for example in FIG. 11, the means for selectively moving the movable divider preferably comprises an electrically actuated solenoid 298 which is connected to divider 292 via a linkage mechanism indicated schematically with the designing numeral 299. Solenoid 298 also can be alternatively actuated pneumatically or hydraulically. Moreover, a pneumatic motor, a hydraulic motor, or a stepper motor can be substituted for the electric solenoid in alternative embodiments of the means for selectively moving the moveable divider. Each of the solenoid embodiments and the alternative motor embodiments is represented schematically in FIG. 11 by the designating numeral 298. Actuation of solenoid 298 or motor 298 moves divider 292 between the first position (shown in solid line in FIG. 11) and the second position (shown in dashed line in FIG. 11).

Figure 12:
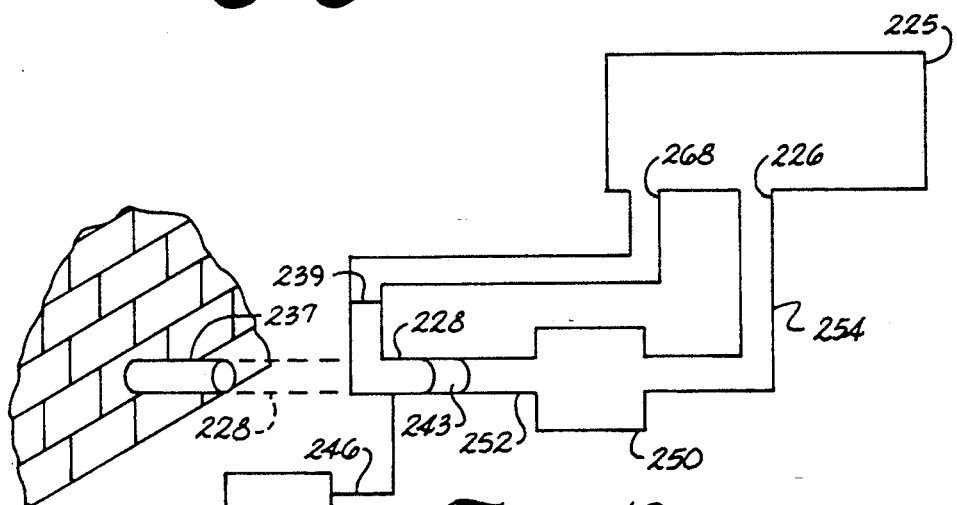
FIG. 12 is a schematic diagram of alternative embodiments of components of an embodiment of the present invention.

An alternative embodiment of the valving means is illustrated for example in FIG. 12 and includes a permanent conduit 254 which connects the outlet of the fluidizing medium supplying means, such as air blower 250, and the second opening 226 of tank 225, an embodiment of the containing means. A connector 228 (shown in solid line in a first position in FIG. 12 and in dashed line in a second position in FIG. 12) selectively communicates with the first opening of the containing means. This communication preferably occurs via an outlet 268 of tank 225 and extends selectively to one of the inlet of an embodiment of the fluidizing medium supplying means, such as the inlet 252 of air blower 250, and a discharge outlet 237, which conducts exhausted fluidizing medium to a remote location, preferably outside the building housing the decontamination units. The odor of the fluidizing medium exhausted from the decontamination unit can be quite offensive, and thus it is desireable to exhaust the fluidizing medium at a location away from operating personnel. The decontamination unit preferably exhausts the fluidizing medium at a location outside of the building that houses the decontamination unit.

This alternative embodiment of the valving means further includes means for selectively connecting the connector to one or the other of the discharge outlet and the inlet of the fluidizing medium supplying means. As embodied herein and shown for example in FIG. 12, the means for selectively connecting the connector preferably comprises a rotatable joint 239 at one end of connector 228. The selectively connecting means further preferably includes a detachable fitting 243 that is configured to selectively form a continuous connection with either the inlet 252 of an embodiment of the fluidizing medium supplying means such as air blower 250 or a free end of discharge outlet 237. Detachable fitting 243 is defined at the opposite end of connector 228 from the end which includes rotatable joint 239.

The selectively connecting means further preferably includes means for rotating the connector about the rotatable joint to position the detachable fitting so as to permit each of the selective formations of the intermediate portion of the connector with one of the discharge outlet or the inlet of the fluidizing medium supply means. As embodied herein and shown for example in FIG. 12, the means for rotating the connector about the rotatable joint preferably includes an electrically actuated solenoid 245 and a linkage mechanism 246 which connects solenoid 245 to connector 228. Solenoid 245 also can be actuated pneumatically or hydraulically instead of electrically. Moreover, alternative embodiments of the means for rotating the connector about the rotatable joint can include a pneumatic motor, a hydraulic motor, or a stepper motor in place of the solenoid. Each of the solenoid embodiments and the alternative motor embodiments is represented schematically in FIG. 12 by the designating numeral 245. Actuation of solenoid 245 or motor 245 effects rotation of connector 228 between the configuration drawn in solid line in FIG. 12 and the dotted line configuration drawn in FIG. 12 for connector 228. In the former, fitting 243 is joined to the inlet 252 of air blower 250. In the dotted line configuration shown in FIG. 12, fitting 243 would be joined to discharge outlet 237.

Figure 12A:
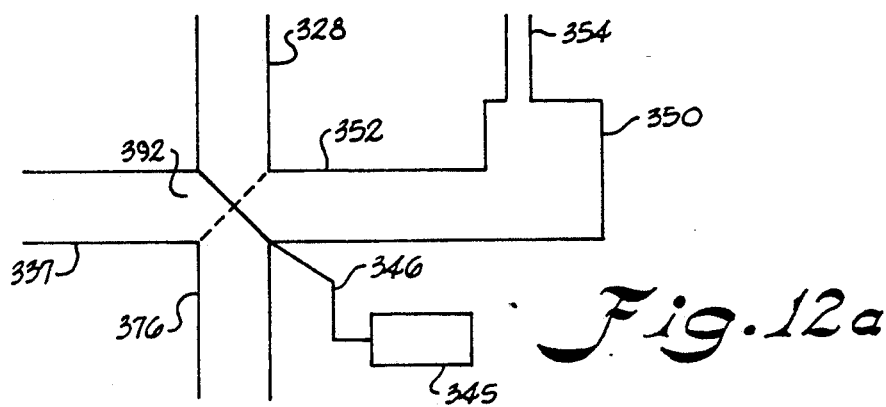
FIG. 12a is a schematic diagram of alternative embodiments of components of an embodiment of the present invention.

FIG. 12a schematically represents an alternative arrangement of the selectively connecting means shown in FIG. 12. As embodied in this alternative embodiment of the selectively connecting means shown in FIG. 12a, a movable stopper 392 is disposed at the junction which forms a connection between connector 328, inlet 352 of air blower 350, ambient inlet 376, and discharge outlet 337. The air blower 350 embodiment of the fluidizing medium supplying means is connected to the tank (not shown) via permanent conduit 354. Ambient inlet 376 communicates with the ambient atmosphere.

Stopper 392 is disposed to move between a recirculating position and an exhaust position. The decontamination unit can operate in the heating mode when stopper 392 assumes the recirculating position and can operate in the cooling mode when stopper 392 assumes the exhaust position. In the recirculating position shown in solid line in FIG. 12a, stopper 392 is positioned to allow communication via connector 328 between inlet 352 of the fluidizing medium supplying means and the first opening (not shown) of the containing means (not shown). In the exhaust position, stopper 392 is positioned as shown in dotted line in FIG. 12a to allow communication via connector 328 between discharge outlet 337 and the first opening (not shown) of the containing means (not shown). The exhaust position orientation (dotted line in FIG. 12a) of stopper 392 also allows communication between the ambient atmosphere and blower 350 via ambient inlet 376 and blower inlet 352.

In the FIG. 12a embodiment, the selectively connecting means further comprises means for selectively moving the movable stopper between the recirculating position and the exhaust position. As embodied herein, the means for selectively moving the stopper can comprise an electrically actuated solenoid 345, and a linkage mechanism 346 connected between the solenoid and stopper 392. The solenoid can be actuated electrically, pneumatically or hydraulically. Alternative embodiments of the means for selectively moving the stopper can include a pneumatic motor, a hydraulic motor, or a stepper motor in place of the solenoid. Each of the solenoid embodiments and the alternative motor embodiments is represented schematically in FIG. 12a by the designating numeral 345. Actuation of solenoid 345 or motor 345 effects movement of stopper 392 between the recirculating position shown in solid line in FIG. 12a and the exhaust position shown in dotted line form in FIG. 12a.

In accordance with the present invention, means are provided for monitoring the temperature inside the containing means. As embodied here and shown for example in FIG. 1, the temperature monitoring means, comprises a temperature probe 102 and a dial thermometer 103. Temperature probe 102 extends through shell 40 and into tank 25 and can provide an electronic signal corresponding to the temperature detected by probe 102. A visual signal can be read from dial thermometer 103 by the operating personnel, and the electronic signal from probe 102 can be supplied as an input to a control mechanism to be described hereinafter.

Dial thermometer 103 preferably comprises a bimetal temperature sensitive element immersed in a fluid. The thermometer should be suitable for continuous service at 145° F. temperatures and preferably be constructed of a stainless steel case and having an easily visible dial on the order of three inches in diameter.

In further accordance with the present invention, means are provided for controlling the actuation of the heating means, the valving means, and the fluidizing medium supplying means according to a predetermined sequence and according to monitored performance of the decontamination apparatus. The control means is connected to the temperature monitoring means. As embodied herein and shown schematically for example in FIG. 10, the control means comprises an electrical control circuit indicated generally by the designating numeral 104. Electrical control circuit 104 can include a switch 105 which can be manipulated in at least three alternative positions. In one position only blower 50 is in operation. In a second position only blower 50 and heater 56 are in operation. In a third configuration of switch 105, neither blower 50 nor heater 56 is in operation.

Electrical control circuit 104 includes a timer 106 which is an electrically powered clock capable of timing at least a twelve hour period and any time period less than the maximum time period capability of timer 106. Electrical control circuit 104 also includes an electrical switching means for electrically permitting timer 106 to control the supply of electrical power to each of the heating means, the valving means, and the fluidizing medium supplying means.

Figure 10:
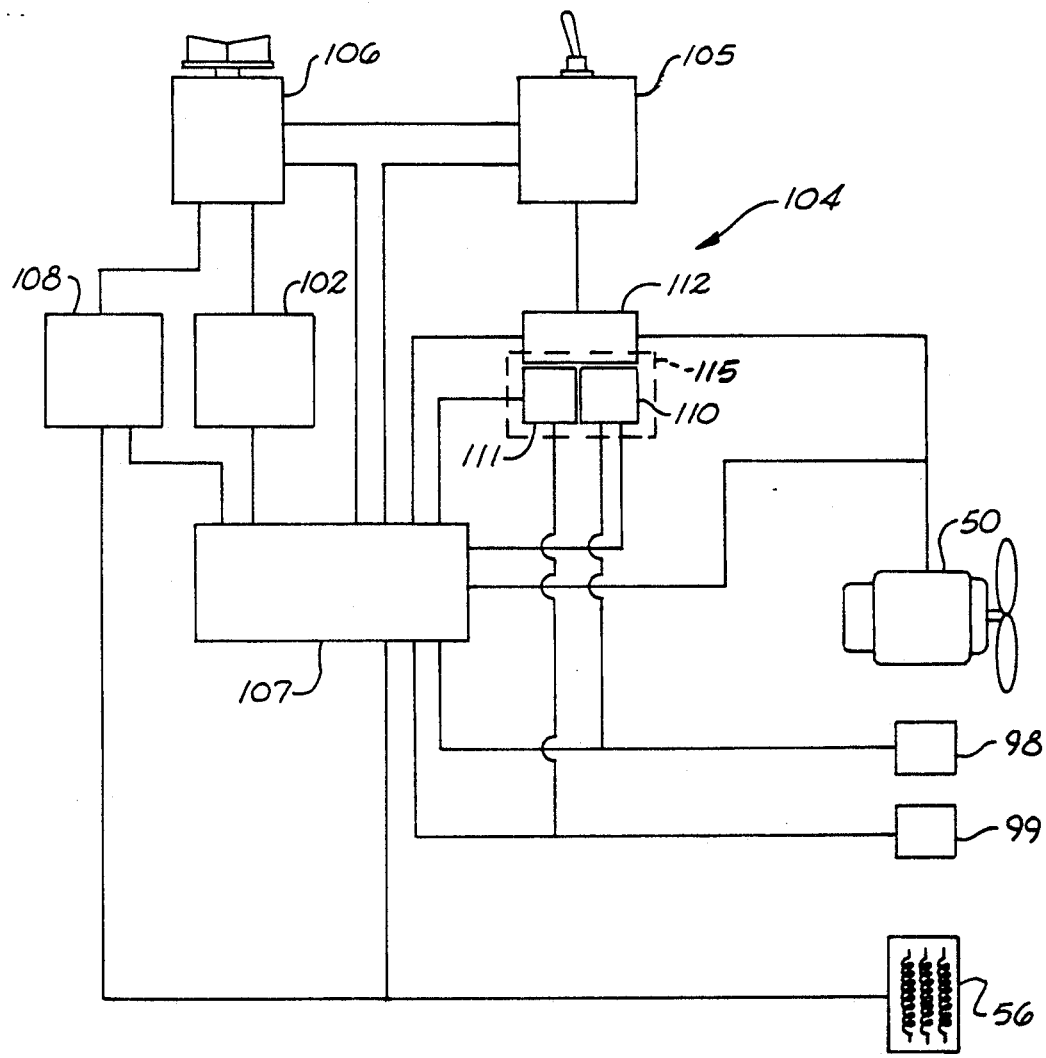
FIG. 10 is a schematic diagram of components of an embodiment of the present invention.

As embodied herein and shown schematically in FIG. 10 for example, the electrical switching means includes at least one electrical relay 108 for the heating means, at least one electrical relay 115 (shown in phantom in FIG. 10) for the valving means, and one electrical relay 112 for the fluidizing medium supplying means. In an alternative embodiment shown in FIG. 10, the electrical switching means includes one electrical relay 110 for solenoid 98 and another electrical relay 111 for solenoid 99 rather than a single electrical relay 115 (shown in phantom in FIG. 10) controlling both solenoids 98, 99 in tandem. Thus, the illustrated embodiment of the electrical switching means permits independent control over each solenoid 98, 99. As shown in FIG. 10, timer 106 is connected to temperature probe 102 and receives electrical signals representative of the temperature being monitored by probe 102. Timer 106 can be connected to a microprocessor unit 107 with its own internal real time clock and which can be programmed to control operation of the decontamination unit according to any predetermined sequence and/or monitoring of temperature of the microspheres during the decontamination process.

Figure 9:
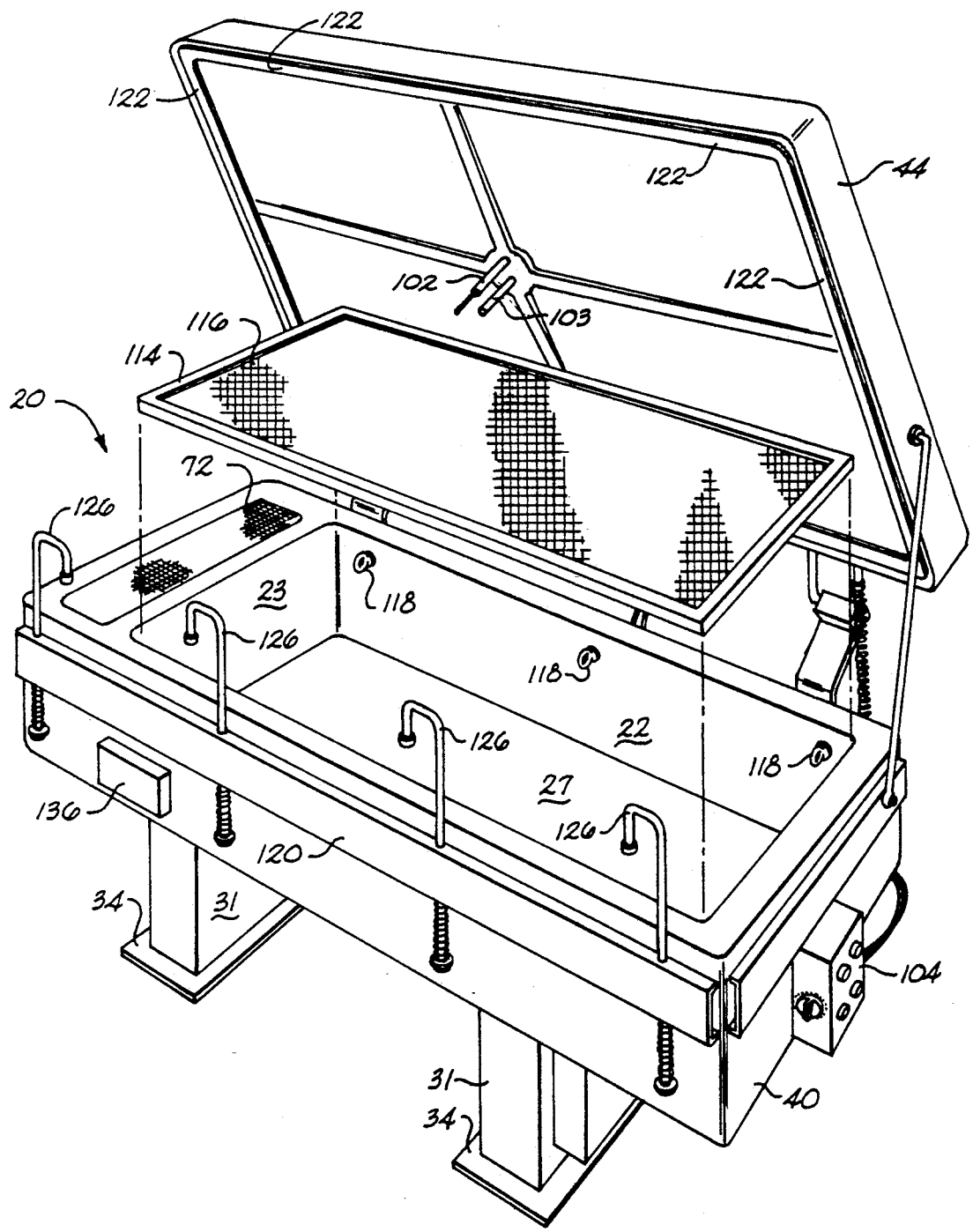
FIG. 9 is a perspective view of an embodiment of the apparatus of the present invention.

In further accordance with the present invention, means are provided for screening the microspheres before they enter the containing means. As embodied herein and shown for example in FIG. 9, the screening means includes a sieving screen 114 which preferably includes a flexible mesh material mounted on a rigid frame extending around the perimeter of the mesh material, which has a plurality of openings 116 therethrough. The size of openings 116 depends upon the size of the clumps of microspheres which are desired to be removed from the batch of contaminated microspheres to be decontaminated. The screening means also includes a plurality of sieve support means mounted to the interior of the containing means for engaging the attachment means. As shown in FIG. 9 for example, the sieve support means can include a plurality of eyelets 118 having a threaded end screwed into the interior of tank sides 22 for engaging the rigid frame of sieving screen 114.

In yet further accordance with the present invention, means are provided for protecting decontamination unit 20 from being damaged by collisions with it at the service centers where numerous mobile hospital beds and other mobile devices are present. Each hospital bed weighs about a ton when carrying a full load of microspheres and thus is capable of producing a significant impact in a collision. As embodied herein and shown for example in FIGS. 1, 3 and 9, the protective means can include a plurality of protective bumpers 120 which are attached around the outside of shell 40 and can comprise a rigid rectangular hollow channel formed of a rigid material such as aluminum or other metal. Bumpers 120 also can include an elastic covering (not shown) to help absorb the shock of collisions.

In further accordance with the present invention, means are provided for sealing the shell cover against the shell to prevent leakage of the microspheres during operation of decontamination apparatus 20 to decontaminate the contaminated microspheres. As embodied herein and shown for example in FIGS. 1, 2, 3 and 9, the means for sealing the decontamination unit against microsphere leakage can include a flexible gasket 122 which is disposed on shell cover 44 around the periphery thereof and is deformable to form an air-tight seal when cover 44 is properly seated under pressure atop shell 40 around shell opening 42. As shown in FIG. 1, the sealing means further includes a spring-biased hooking device 124 which is attached to the upper portion of hinges 48 to pull cover 44 and gasket 122 snugly against the edge of shell 40 that carries hinges 48. As shown in FIGS. 1, 3 and 9, the sealing means also can include a plurality of J-shaped spring-actuated clamping members 126 that press the cover and gasket against the shell in the vicinity of the shell's edge opposite the edge carrying the hinges. This is the edge of cover 44 that moves away from shell 40 when cover 44 is lifted open. Each clamping member 126 includes a J-bar 128. As shown in FIG. 3 for example, J-bar 128 has one end fitted through two opposite holes drilled into bumpers 120 and has a spring 130 disposed along the straight end of J-bar 128 and between bumper 120 and a capping nut 132 which can be screwed to increase the pressure applied by the opposite (J-shaped) end of J-bar 128 to the top of cover 44 and thus improve the seal between cover 44, gasket 122, and shell 40.

As noted above, embodiments of the valving means such as valve 74 are designed so as to provide less than air-tight operation in order to provide a release for the build-up of pressure occasioned when the fluidizing medium is heated. Were it not for this pressure release mechanism, the build-up of pressure might cause leakage past gasket 122. Such leakage could result in the spillage of contaminated or partially contaminated microspheres into the environment of the personnel attending the decontamination unit, and thus would be undesirable. Accordingly, the less than air-tight configuration of the embodiments of the valving means can be considered to constitute a feature of the means provided for sealing the shell cover against the shell to prevent leakage of the microspheres during operation of the decontamination apparatus to decontaminate the contaminated microspheres.

As shown for example in FIG. 1, a prop rod 134 can be disposed for holding cover 44 in an open position. Prop rod 134 is pivotally mounted to shell 40 and cover 44. Prop rod 134 can be detachably mounted to cover 44 so as to be removable from cover 44 when it is desired to close cover 44 onto shell 40. In this way, prop rod 134 is disposed for storage when cover 44 is in a closed position.

In further accordance with the present invention, means are provided for continuously documenting the temperature being monitored by the temperature monitoring means. As embodied herein and shown for example in FIG. 9, the means for documenting the temperature can include a recorder 136, which provides a paper tape copy of the continuously monitored temperature on a scale which can be calibrated by operating personnel. Recorder 136 can be electrically connected to temperature probe 102 to receive signals therefrom indicative of the temperature being monitored by probe 102. In an alternative embodiment of the documenting means shown schematically in FIG. 10 for example, temperature probe 102 sends electronic signals to a microprocessor unit 107, which is included in electrical control circuit 104, and this input is stored in the memory of the electronic microprocessor and can be printed in readable fashion on a paper copy.

In accordance with the method of the present invention for decontaminating contaminated microspheres of a patient support system employing a fluidizing medium to fluidize the microspheres to provide support for the patient, the following steps are provided. The contaminated microspheres are sieved. The sieved contaminated microspheres are introduced into a container so as to isolate the microspheres from physical contact with the environment during the decontamination method. A fluidizing medium is heated, and the microspheres are fluidized by introducing the heated fluidizing medium into the container. Heat is transferred from the heated fluidizing medium to the microspheres to heat the microspheres and maintain their temperature at no less than 55° C. for a predetermined period of time. The heated fluidizing medium is recirculated into and out of the container to conserve heat energy during heat decontamination of the microspheres. After the predetermined period of time has elapsed, the microspheres are cooled. The microspheres preferably are maintained at a minimum holding temperature selected to prevent condensation of moisture on the microspheres. The decontamination process preferably is documented by continuously monitoring the temperature inside the container during the decontamination of the microspheres and recording this monitored temperature versus time.

The preferred means of carrying out the method of the present invention is performed by the apparatus of the present invention described above. For example, the contaminated microspheres preferably are sieved by using a sieving screen 114 having its rigid frame resting atop eyelets 118 as shown in FIG. 8. Sieving screen 114 is provided with a plurality of openings 116 sized to remove clumps of contaminated microspheres larger than a predetermined size. Preferably, clumps of microspheres larger than one-eighth (⅛) of an inch in diameter are removed by sieving screen 114.

The microspheres are introduced into a container preferably by sieving them over tank 25 so that the microspheres to be decontaminated pass through openings 116 of sieving screen 114 and fall into tank 25. The microspheres are fluidized by activating gas blower 52 and configuring valve 74 so as to provide air through second opening 26 of tank 25. Air then passes through diffuser board 27 and fluidizes the microspheres held inside tank 25.

The fluidizing medium preferably is heated prior to its entry into tank 25 so that the heated fluidizing medium can transfer heat to the microspheres inside tank 25 to raise their temperature to an appropriate temperature for decontamination. Heating the microspheres by fluidizing them with a pre-heated fluidizing medium is preferable over immersing a heating element in the midst of the microspheres. The immersion heating method suffers from the disadvantages noted above. The heating method of the present invention provides a more efficient heat transfer to the microspheres, no damage to the microspheres from heating, better heat distribution within the mass of fluidized microspheres during the decontamination process, and more reliable temperature monitoring of the microspheres.

The appropriate decontamination temperature depends upon the period of time at which the microspheres are to be maintained at the predetermined temperature. The following temperature/time pairings have been determined to be effective for decontamination of the microspheres in a safe and effective manner for all contaminants encountered to date:

(1) 55° C. and 24 hours;
(2) 65° C. and 12 hours;
(3) 70° C. and 8 hours;
(4) 75° C. and 4 hours;
(5) 80° C. and 4 hours;
(6) 85° C. and 2 hours; and
(7) 90° C. and 1 hour.

The fluidizing medium preferably is recirculated into and out of tank 25 to conserve heat energy during heat decontamination of the microspheres. This is preferably accomplished by appropriate reconfiguration of valve 74 as described above in the heating mode of operation.

After the predetermined period of time elapses, the microspheres preferably are cooled by ceasing heating of the fluidizing medium, ceasing recirculation of the heated fluidizing medium, introducing ambient air or refrigerated air into the container to fluidize the microspheres, and expelling the heated fluidizing medium to the atmosphere outside of the premises housing the decontamination unit. The fluidizing medium carries undesirable odors picked up from the contaminated microspheres, and thus discharge of this fluidizing medium in the vicinity frequented by operating personnel for the decontamination unit is to be avoided. This avoidance preferably is accomplished by routing the exhausted fluidizing medium to a location outside of the building housing the decontamination units. As the ambient air fluidizes the microspheres during the cooling process, the ambient air becomes heated by heat transfer from the microspheres to the air. The cooling process preferably is accomplished by configuring valve 74 in the cooling mode of operation as described above.

The decontamination method of the present invention further includes another alternative mode of operation that maintains the microspheres at a predetermined minimum holding temperature after the microspheres have been heat decontaminated and cooled to the minimum holding temperature. Maintaining the microspheres at the minimum holding temperature can be accomplished by configuring valve 74 as in the heating mode of operation, but discontinuing heating of the fluidizing medium when the temperature of the microspheres rises above the holding temperature and resuming heating the fluidizing medium when the temperature of the microspheres falls below the holding temperature. The holding temperature is preselected depending upon anticipated ambient atmospheric conditions, such as pressure, humidity, and temperature, so as to prevent adsorption of moisture from the ambient air onto the microspheres.

The alternating heating and cessation of heating of the fluidizing medium according to the temperature of the microspheres can be accomplished by using electrical control circuit 104 to control actuation of the valve switching means, the heating means, and the fluidizing medium supplying means. Accordingly, microprocessor 107 or timer 106 can be programmed for the predetermined time period depending upon the minimum temperature maintained inside tank 25 during the decontamination process. As soon as the predetermined time has elapsed, timer 106 can be programmed to actuate reconfiguration of valve 74 into the cooling mode of operation. Once temperature probe 102 detects that the minimum holding temperature has been attained, control circuit 104 can reconfigure valve 74 to the heating mode of operation, while switching off heater 56. In this way, the air inside tank 25 continues to be recirculated, but the air is no longer heated by heater 56 prior to reentering tank 25. When temperature probe 102 detects that the temperature inside tank 25 has fallen below the minimum holding temperature, then control circuit 104 can actuate heater element 62, and gas blower 50 recirculates the heated air. When the heating mode of operation returns the temperature of the microspheres to the minimum holding temperature, then electrical control circuit 104 can once again switch off heater element 62. This same procedure can be continued indefinitely or can be programmed by timer 106 to cease at a predetermined time from the beginning of this holding mode of operation or from any other event during the course of the decontamination process. Moreover, this temperature maintenance process can be followed when timer 106 includes programmable electronic microprocessor unit 107.

It will be apparent to those skilled in the art that various modifications and variations can be made in the apparatus and method for bead decontamination of the present invention without departing from the scope or spirit of the invention. Thus, it is intended that the present invention cover the modifications and variations of this invention provided they come within the scope of the appended claims and their equivalents.

What is claimed is:

1. An apparatus for decontaminating contaminated microspheres of a patient support system employing a fluidizing medium to fluidize the microspheres to provide support for the patient, the apparatus comprising:
    (a) means for containing the microspheres during decontamination of same, said containing means having a first opening therethrough to permit loading of the microspheres into the containing means, said containing means further including a bottom and a second opening through which passage of air is directed to fluidize the microspheres at least during decontamination of same, said second opening being disposed generally in said bottom of said containing means;
    (b) means for separating said bottom of said containing means from the microspheres and for permitting diffusion of a fluidizing medium therethrough for fluidizing the microspheres, said separating means being disposed generally between said first and second openings to separate said openings from each other;
    (c) means for supporting the containing means;
    (d) means for heat-insulating the containing means;
    (e) means for shielding the personnel operating the apparatus from direct physical contact with the outside facing surfaces of the containing means and heat-insulating means;
    (f) means for supplying a fluidizing medium through said second opening in said containing means, said fluidizing medium supplying means having an inlet for receiving gas therethrough and having an outlet communicating with said second opening in said containing means;
    (g) means for heating said fluidizing medium prior to passage of same through said second opening of said containing means;
    (h) means for recirculating said fluidizing medium to said supplying means after said fluidizing medium passes through said containing means, said recirculating means having an outlet;
    (i) means for preventing microspheres from being recirculated along with said fluidizing medium;
    (j) means for valving said fluidizing medium for at least two alternative modes of operation, wherein during a first mode of operation, heated fluidized medium is received from said recirculating means and routed to said supplying means, and during a second mode of operation, said fluidizing medium received from said recirculating means is expelled from the decontamination apparatus and an alternative source of fluidizing medium is routed to said fluidizing medium supply means;
    (k) means for monitoring the temperature inside said containing means; and
    (l) means for controlling individual actuation of each of said fluidizing medium supplying means, said heating means, and said valving means according to a predetermined sequence and according to monitored performance of the apparatus, said temperature monitoring means being connected to said actuation control means to furnish signals indicative of the temperature measured by said temperature monitoring means.

2. An apparatus as in claim 1, wherein:
said containing means comprises a tank having a bottom, sides, and said sides defining an open top of said tank.

3. An apparatus as in claim 1, wherein:
said separating means comprises a diffuser board disposed in said containing means above said bottom and forming a plenum between said diffuser board and said bottom of said containing means.

4. An apparatus as in claim 3, further including:
resin applied to the surface of said diffuser board intended to contact the decontaminated microspheres.

5. An apparatus as in claim 3, further including:
resin applied to the surface of said diffuser board facing toward said first opening and away from said second opening.

6. An apparatus as in claim 1, wherein:
said supporting means comprises a stand having at least one base member for resting on the floor, said stand for receiving said containing means and supporting said containing mean at a predetermined height above said base member.

7. An apparatus as in claim 6, wherein:
said supporting means further comprises a plurality of support sleeves for transferring the weight of said containing means and any microspheres contained therein to said stand while reducing any conductive heat transfer between said containing means and said stand, one end of each said sleeve contacting a narrow portion of the surface of said containing means.

8. An apparatus as in claim 1, wherein:
said heat-insulating means for said containing means comprises a heat insulation blanket surrounding said containing means and being attached thereto and further comprising a heat insulation board disposed between the bottom of said containing means and said supporting means to thermally isolate said containing means from said supporting means.

9. An apparatus as in claim 1, wherein:
said shielding means comprises a rigid shell formed of heat-insulating material,
said shell being configured to cover said containing means and said insulating means,
said shell defining a shell opening at the top thereof to expose said first opening of said containing means,
said shielding means further comprising a cover, said cover being heat-insulated and configured to cover said shell opening,
said shielding means further comprising at least one hinge attached to said cover and said shell for facilitating opening and closing said cover.

10. An apparatus as in claim 9, wherein:
said recirculating means comprises a gas recirculation channel defined in said shell and connecting said first opening of said containing means into communication with said fluidizing medium supplying means.

11. An apparatus as in claim 9, further comprising:
a prop rod disposed for holding said cover in an open position and further disposed for storage when said cover is in a closed position.

12. An apparatus as in claim 9, further comprising:
means for sealing said cover against said shell to prevent leakage of microspheres during operation of the apparatus to decontaminate the contaminated microspheres.

13. An apparatus as in claim 12, wherein:
said sealing means comprises:
 (i) a flexible gasket disposed around the periphery of said cover to rest atop said shell around said shell opening,
 (ii) at least two J-shaped, screw-actuated clamping members for pressing said gasket and said cover against said shell in the vicinity of the edge opposite the edge carrying said hinges, and
 (iii) a spring-biased hooking device for pressing said cover and said gasket against said shell around the edge of said shell carrying said hinges.

14. An apparatus as in claim 1, wherein:
said fluidizing medium supplying means comprises a gas blower having a gas inlet for receiving air therethrough and having a gas outlet connected in communication with said second opening of said containing means.

15. An apparatus as in claim 1, wherein:
said heating means comprises an air heater member having an outlet for heated air being connected to said second opening of said containing means and having an air inlet for receiving air to be heated.

16. An apparatus as in claim 1, wherein:
said means for preventing microspheres from being recirculated along with the fluidizing medium comprises a filter disposed for preventing microspheres from moving through said air recirculation channel.

17. An apparatus as in claim 16, wherein:
said means for preventing microspheres from being recirculated along with the fluidizing medium further comprises means for restricting the flow of fluidizing medium exiting said first opening of said containing means.

18. An apparatus as in claim 17, wherein:
said means for restricting the flow of fluidizing medium comprises a narrow slot disposed between said first opening of said containing means and said air recirculation channel and at a location such that the fluidizing medium must pass through said slot before engaging said filter.

19. An apparatus as in claim 1, wherein:
said valving means comprises:
 (i) a permanent conduit connecting said outlet of said fluidizing medium supplying means and said second opening in said containing means;
 (ii) a connector selectively communicating between said first opening of said containing means and one of said fluidizing medium supplying means inlet and a discharge outlet, said discharge outlet for carrying away fluidizing medium exiting said containing means and discharging same at a location remote from the decontamination apparatus; and
 (iii) means for selectively connecting said connector to one of said fluidizing medium supplying means inlet and said discharge outlet.

20. An apparatus as in claim 19, wherein:
said selectively connecting means comprises:
 (i) a rotatable joint at one end of said connector;
 (ii) a detachable fitting defined at an opposite end of said connector, said detachable fitting being configured to form a continuous connection between said connector and selectively one of said discharge outlet and an inlet of said fluidizing medium supplying means; and
 (iii) means for rotating said connector about said rotatable joint to position said detachable fitting to permit each of said selective connections of said connector.

21. An apparatus as in claim 20, wherein:

said means for rotating said connector comprises a solenoid.

22. An apparatus as in claim 20, wherein:
said means for rotating said connector comprises a motor.

23. An apparatus as in claim 19, wherein:
said selectively connecting means comprises:
  (i) a movable stopper, said stopper being disposed to move between a recirculating position and an exhaust position, said recirculating position allowing communication between said inlet of said fluidizing medium supplying means and said first opening of said containing means, said exhaust position allowing communication between said first opening of said containing means and said discharge outlet; and
  (ii) means for selectively moving said movable stopper between said recirculating position and said exhaust position.

24. An apparatus as in claim 23, wherein:
said means for selectively moving said stopper comprises a solenoid.

25. An apparatus as in claim 23, wherein:
said means for selectively moving said stopper comprises a motor.

26. An apparatus as in claim 1, wherein:
said valving means comprises:
  (i) a valve having at least four air flow access conduits, a first one of said conduits being dedicated for receiving ambient air, a second one of said conduits being dedicated for expelling air from said containing means to the ambient atmosphere, a third one of said conduits communicating with said gas inlet of said fluidizing medium supplying means, a fourth one of said conduits communicating with said outlet of said recirculating means, and
  (ii) means for switching said valve between a heating mode of operation and a cooling mode of operation, said heating mode including configuring said valve to connect said fourth air flow access conduit to said third air flow access conduit, said cooling mode including configuring said valve to connect said first conduit to said third conduit and connecting said fourth conduit to said second conduit.

27. An apparatus as in claim 26, wherein:
said valve switching means includes:
  (i) a valve passage having an opening at opposite ends thereof;
  (ii) a pair of cover plates, one of said cover plates being disposed near each end of said valve passage;
  (iii) a pair of connecting members, each connecting member having one end connected to one of said cover plates;
  (iv) a pair of electrically actuatable solenoids, each solenoid connected to an opposite end of one of said connecting members;
  (v) means for biasing each said cover plate at a position away from said respective nearby end of said valve passage; and
  (vi) wherein actuation of each said solenoid causes each respective cover plate to cover each respective nearby end of said valve passage to prevent flow of gas therethrough and thereby change the gas flow configuration of said valve.

28. An apparatus as in claim 27, wherein:
said biasing means for each said cover plate comprises a spring attached at one end to each cover plate.

29. An apparatus as in claim 26, wherein:
said valve switching means comprises:
  (i) a movable divider, said divider being disposed to move between a first position and a second position, said first position allowing communication between said first conduit and said second conduit and between said third conduit and said fourth conduit, said second position allowing communication between said first conduit and said third conduit and between said second conduit and said fourth conduit; and
  (ii) means for selectively moving said movable divider between said first position and said second position.

30. An apparatus as in claim 29, wherein:
said means for selectively moving said movable divider comprises a solenoid.

31. An apparatus as in claim 29, wherein:
said means for selectively moving said movable divider comprises a motor.

32. An apparatus as in claim 1, wherein said actuation control means comprises a control circuit.

33. An apparatus as in claim 32, wherein: said control circuit includes a timer and electrical switching means for electrically permitting said timer to control the supply of electrical power to each of said heating means, said valving means, and said fluidizing medium supplying means.

34. An apparatus as in claim 33, wherein said electrical switching means includes at least one electrical relay for each of said heating means, said fluidizing medium supplying means, and said valving means.

35. An apparatus as in claim 1, wherein:
said temperature monitoring means comprises a temperature probe disposed to project inside said containing means.

36. An apparatus for decontaminating contaminated microspheres of a patient support structure employing a medium to fluidize the microspheres to provide support for the patient, the apparatus comprising:
  (a) a tank, said tank having a bottom, two opposite sides, two opposite ends, and said sides and ends defining an open top of said tank;
  (b) a diffuser board disposed in said tank above said tank bottom and forming a plenum between said diffuser board and said tank bottom, said diffuser board for supporting a mass of contaminated microspheres thereon and for permitting passage of the fluidizing medium therethrough;
  (c) a stand having a base member for resting on the floor, said stand for receiving said tank and supporting said tank at a predetermined height above said base member;
  (d) a heat insulation blanket surrounding the exterior of said sides and ends of said tank and being attached thereto;
  (e) a heat insulation board disposed between said bottom of said tank and said stand to thermally isolate said tank from said stand;
  (f) a rigid shell formed of heat-insulating material, said shell being configured to cover said ends and sides of said tank and said insulation blanket surrounding same, said shell defining a shell opening at the top thereof to expose said open top of said tank;

(g) a cover, said cover being heat-insulated and configured to cover said shell opening;
(h) at least one hinge attached to said cover and said shell for facilitating hinged opening and closing of said cover;
(i) a prop rod disposed for holding said cover in an open position and for storage when said cover is in a closed position;

(j) means for sealing said cover against said shell to prevent leakage of microspheres during operation of the apparatus to decontaminate the contaminated microspheres;

(k) a heat-insulated entrance passage connected at one end to said plenum;

(l) an air heater member having an outlet for heated air, said outlet being connected to said entrance passage, said heater member further having an air inlet for receiving air to be heated;

(m) a valve having at least four air flow access conduits, one of said conduits being dedicated for receiving ambient air, a second of said conduits being dedicated for expelling air from said tank to the ambient atmosphere;

(n) an air blower having an air inlet communicating with a third air flow access conduit of said valve and having an air outlet communicating with said air inlet of said heater;

(o) an air recirculation channel defined in said shell and connecting said open top of said tank to a fourth air flow access conduit of said valve;

(p) a filter disposed for preventing microspheres from moving through said air recirculating channel;

(q) means for switching said valve between a heating mode of operation and a cooling mode of operation, said heating mode including configuring said valve to connect said fourth air flow access conduit to said third air flow access conduit, said cooling mode including configuring said valve to connect said first conduit to said third conduit and connecting said fourth conduit to said second conduit;

(r) means for monitoring the temperature inside said tank;

(s) means for controlling actuation of said blower, heater and valve according to a predetermined sequence and according to monitored performance of the apparatus, said temperature monitoring means being connected to said control means to furnish signals indicative of the temperature measured by said temperature monitoring means;

(t) means for screening microspheres before entry of said microspheres into said tank, said screening means being mountable in said tank near said open top of said tank; and (u) a plurality of protective bumpers being mounted around a predetermined outside-facing periphery of said shell.

37. An apparatus as in claim 36, wherein switching means includes:

(i) a valve passage having an opening at opposite ends thereof;

(ii) a pair of cover plates, one said cover plate being disposed near each end of said valve passage;

(iii) a pair of connecting members, each connecting member having one end connected to one of said cover plates;

(iv) a pair of electrically actuatable solenoids, each solenoid connected to an opposite end of one of said connecting members;

(v) means for biasing each said cover plate at a position away from said respective nearby end of said valve passage; and (vi) wherein actuation of each said solenoid causes each respective cover plate to cover respective nearby end of said valve passage to prevent flow of gas therethrough and thereby change the gas flow configuration of said valve.

38. An apparatus as in claim 37, wherein:

said means for biasing each said cover plate comprises a spring having one end attached to each respective cover plate.

39. An apparatus as in claim 36, wherein:

said sealing means comprises a spring-biased hooking device for pressing said cover against said shell around said edge of said cover carrying at least one said hinge, and at least two J-shaped, screw-actuated clamping members for pressing said cover against said shell in the vicinity of the edge opposite the edge against said shell carrying at least one said hinge.

40. An apparatus as in claim 36, herein:

said means for actuation control includes an electric control circuit.

41. An apparatus as in claim 36, wherein:

said means for temperature monitoring inside said tank comprises a temperature probe.

42. An apparatus as in claim 36, wherein said means for screening microspheres before entry of same into said tank comprises:

(i) a fine mesh sheet mounted on a rigid frame around the periphery thereof, and (ii) means for supporting said rigid frame above said bottom of said tank, said frame support means being mounted to said interior of said tank and for engaging said rigid frame.

* * * * *